(12) United States Patent
Hoffman et al.

(10) Patent No.: US 8,001,097 B2
(45) Date of Patent: Aug. 16, 2011

(54) COMPUTERIZED SYSTEM AND METHOD FOR BUILDING A SYSTEM OF TEST COMPONENTS FOR A HEALTHCARE ORDERABLE PROCEDURE

(75) Inventors: Mark A. Hoffman, Lees Summit, MO (US); Kevin M. Power, Pleasant Valley, MO (US); Ginger H. Kuhns, Liberty, MO (US); Nicholas Smith, Overland Park, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

(21) Appl. No.: 12/626,270

(22) Filed: Nov. 25, 2009

(65) Prior Publication Data

US 2010/0076781 A1    Mar. 25, 2010

Related U.S. Application Data

(63) Continuation of application No. 11/028,379, filed on Jan. 3, 2005, now Pat. No. 7,634,359.

(51) Int. Cl.
*G06F 7/00* (2006.01)
(52) U.S. Cl. .............. 707/700; 702/19; 702/20; 703/11; 435/5
(58) Field of Classification Search .................... None
See application file for complete search history.

(56) References Cited

U.S. PATENT DOCUMENTS

| | | | |
|---|---|---|---|
| 7,024,399 B2 * | 4/2006 | Sumner et al. | 706/45 |
| 7,260,480 B1 * | 8/2007 | Brown et al. | 702/19 |
| 2004/0014097 A1 * | 1/2004 | McGlennen et al. | 435/6 |
| 2005/0108049 A1 * | 5/2005 | Ram et al. | 705/2 |

* cited by examiner

*Primary Examiner* — Mary Zeman
(74) *Attorney, Agent, or Firm* — Shook Hardy & Bacon

(57) ABSTRACT

A computerized system and method of building a system of test components for an orderable healthcare procedure is provided. An orderable healthcare procedure is received and associated with a discrete ontology concept. An ontology is traversed for the discrete ontology concept to identify test components related to the discrete ontology concept. The test components related to the discrete ontology concept are identified.

20 Claims, 9 Drawing Sheets

| TASK/ASSAY BATCH BUILD | | | |
|---|---|---|---|
| CONCEPTS: | ORDER CATALOG SETTINGS | | |
| ☑ RET.C.1825T>G | DEPT NAME: | LONG DESCRIPTION: | |
| ☐ RET.C.1826G>A | RET SCREENING | RET SCREENING | |
| ☑ RET.C.1826G>T | ACTIVITY TYPE: | CONCEPT: | |
| ☐ RET.C.1831T>C | HELIX | (gDNA).RET | |
| ☑ RET.C.1832G>C | BIOLOGICAL CATEGORY: | | |
| ☐ RET.C.1833C>G | INHERITED | ASSOCIATED TASK/ASSAYS | |
| ☑ RET.C.1852T>A | | | |
| ☐ RET.C.1852T>C | TASK/ASSAY SETTINGS | | |
| ☐ RET.C.1852T>G | ACTIVITY TYPE: | RESULT PROCESSING TYPE: | |
| ☐ RET.C.1853G>A | HELIX | COPY 1 | |
| ☑ RET.C.1853G>T | RESULT TYPE: | CODE SET: | |
| ☐ RET.C.1858T>C | ALPHA | (NONE) | |
| ☐ RET.C.1859G>A | | | |
| ☐ RET.C.1859G>T | | | |
| ☐ RET.C.1900T>C | | | |
| ☐ RET.C.1900T>G | | | |
| ☐ RET.C.1901G>A | | | |

ADD  REMOVE  UPDATE

TASK/ASSAY PREVIEW:

| ACTIVITY TYPE | RESULT PROCESSING TYPE | RESULT TYPE | CODE SET | CONCEPTS |
|---|---|---|---|---|
| HELIX | COPY 1 | ALPHA | (NONE) | RET.C.1825T>G<br>RET.C.1826G>T<br>RET.C.1832G>C<br>RET.C.1852T>A<br>RET.C.1853G>T |
| HELIX | COPY 2 | ALPHA | (NONE) | RET.C.1825T>G |

BUILD  CANCEL

FIG. 9.

COMPUTERIZED SYSTEM AND METHOD FOR BUILDING A SYSTEM OF TEST COMPONENTS FOR A HEALTHCARE ORDERABLE PROCEDURE

CROSS-REFERENCE TO RELATED APPLICATIONS

This application is a continuation of U.S. Ser. No. 11/028,379, filed on Jan. 3, 2005, the disclosure of which is hereby incorporated by reference. This application is related to commonly assigned U.S. application Ser. No. 11/028,262, filed Jan. 3, 2005, the disclosure of which is hereby incorporated by reference in its entirety herein.

STATEMENT REGARDING FEDERALLY SPONSORED RESEARCH OR DEVELOPMENT

Not applicable.

TECHNICAL FIELD

The present invention relates generally to the field of computer software. More particularly, the invention relates to a system and method for building a system of test components for a healthcare orderable procedure.

BACKGROUND

An ontology is a semantically structured controlled vocabulary. Currently, ontologies of molecular biological interest are oriented toward the research community. These ontologies focus primarily on functional attributes of molecular entities and do not meet the requirements for use in the clinical community, such as healthcare organizations, hospitals, physician's offices and clinical healthcare laboratories. The research ontologies do not represent the molecular entities targeted by the tests currently performed in clinical diagnostics in a standardized and machine readable format.

Furthermore, designing and implementing a computerized medical records system is a lengthy and complex process that is currently performed manually. Currently, a database administrator must manually determine the proper individual molecular diagnostic tests to be associated with an orderable procedure. A system and method for automatically proposing molecular diagnostic test components to be associated with an orderable procedure would also be beneficial.

SUMMARY

In one embodiment of the present invention, a method of building a system of test components for an orderable healthcare procedure is shown. An orderable healthcare procedure is received and associated with a discrete ontology concept. An ontology is traversed for the discrete ontology concept to identify test components related to the discrete ontology concept. The test components related to the discrete ontology concept are identified.

In another embodiment of the present invention, a computerized system for building a system of test components for a orderable healthcare procedure is provided. The system comprises a receiving component for receiving an orderable healthcare procedure and an associating component for associating the orderable healthcare procedure with a discrete ontology concept. The system further comprises a traversing component traversing an ontology for the discrete ontology concept to identify test components related to the discrete ontology concept and an identifying component for identifying test components related to the discrete ontology concept.

In yet another embodiment of the present invention, a computerized system of building a system of test components for an orderable procedure is provided. The system comprises means for receiving an orderable healthcare procedure and means for associating the orderable healthcare procedure with a discrete ontology concept. The system further comprises means for traversing the ontology for the discrete ontology concept to identify test components related to the discrete ontology concept and means for identifying test components related to the discrete ontology concept.

BRIEF DESCRIPTION OF THE SEVERAL VIEWS OF THE DRAWINGS

The present invention is described in detail below with reference to the attached drawing figures, wherein:

FIG. 9 is a screen displaying an automatic build system for the orderable procedure comprising likely results or test components for the orderable in accordance with an embodiment of the present invention.

DETAILED DESCRIPTION OF THE INVENTION

Figure 1:
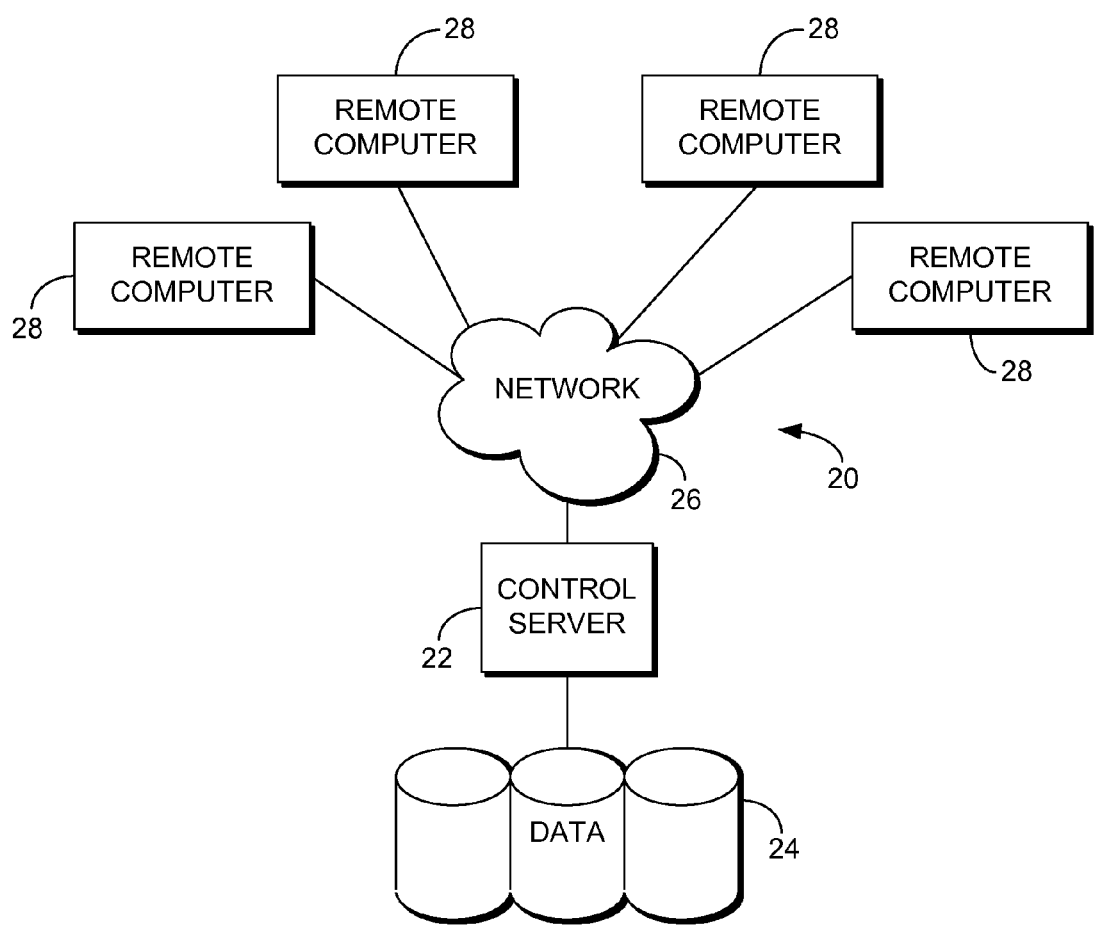
FIG. 1 is a block diagram of a computing system environment suitable for use in implementing the present invention.

With reference to FIG. 1, an exemplary medical information system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes or has access to a variety of computer readable media, for instance, database cluster 24.

Computer readable media can be any available media that can be accessed by server 22, and includes both volatile and nonvolatile media, removable and non-removable media. By way of example, and not limitation, computer readable media may comprise computer storage media and communication media. Computer storage media includes volatile and non-volatile, removable and non-removable media implemented in any method or technology for storage of information, such as computer readable instructions, data structures, program modules, or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared, and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home healthcare environment. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, laboratory experts, genetic counselors, researchers, veterinarians, students, and the like. The remote computers may also be physically located in non-traditional medical care environments so that the entire healthcare community is capable of integration on the network. Remote computers 28 may be a personal computer, server, router, a network PC, a peer device, other common network node healthcare device or the like, and may include some or all of the elements described above relative to server 22. The devices can be personal digital assistants, or other like devices. Computer network 26 may be a local area network (LAN) and/or a wide area network (WAN), but may also include other networks including Internet networks via wired or wireless capability. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. By way of example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Commands and information may also be sent directly from a remote healthcare device to the server 22. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a WINDOWS operating system, operating in conjunction with an Internet-based system, one skilled in the art would recognize that the method and system can be implemented in any system supporting building a system of test components for a healthcare orderable procedure. As contemplated by the language above, the methods and systems of the present invention may also be implemented on a stand-alone desktop, personal computer, or any other computing device used in a medical environment or any of a number of other locations.

Figure 2:
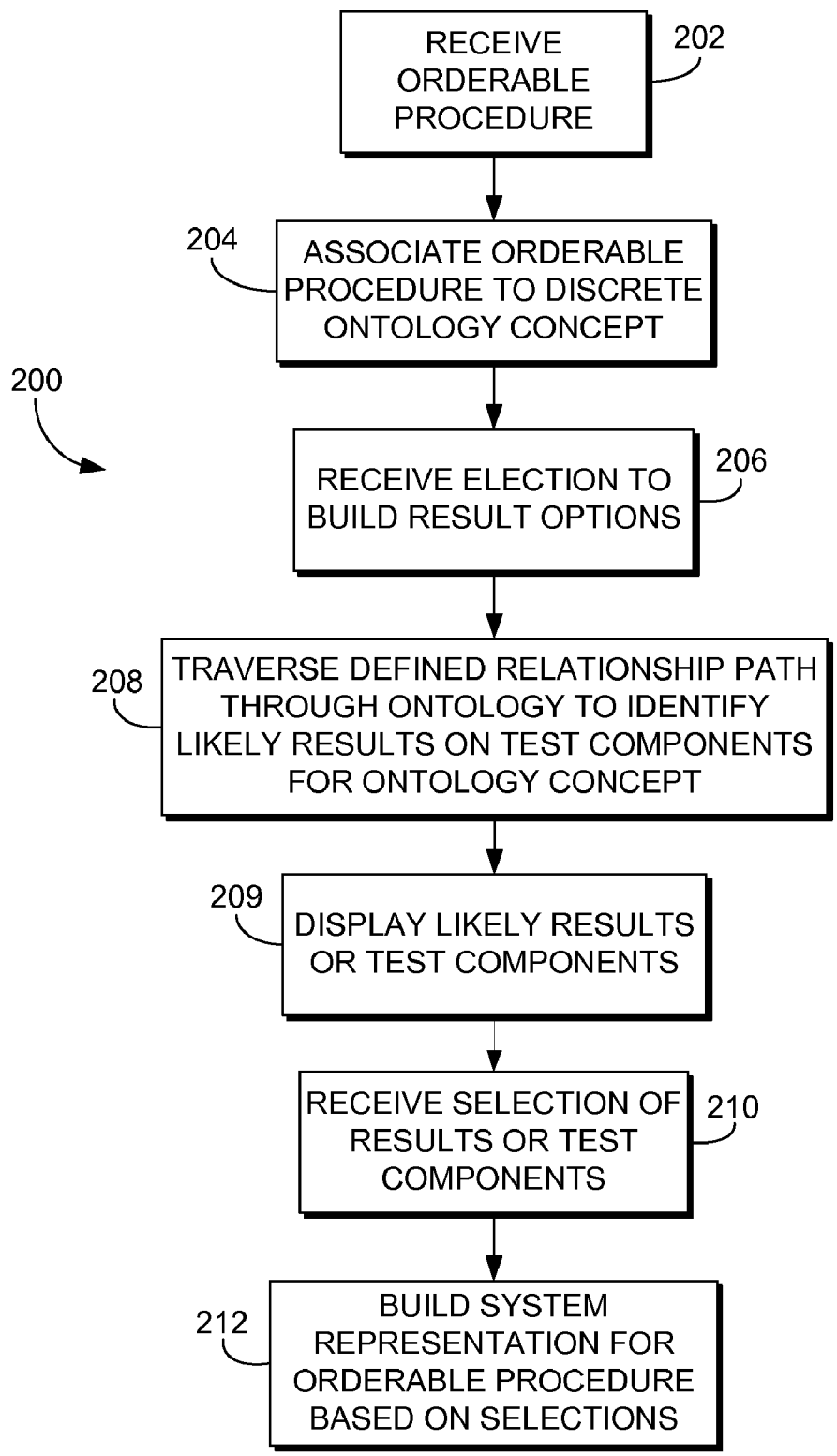
FIG. 2 is a flow diagram of a method for traversing defined relationship paths in an ontology and building a system for an orderable procedure of results or test components in accordance with an embodiment of the present invention.

With reference to FIG. 2, a method 200 for building a system of test components for an orderable procedure is shown. An orderable procedure includes tests, screenings, medications or other clinically significant items or processes that can be ordered by a clinician or other healthcare provider. The method can be applied to a variety of domains, both clinical and non-clinical. This method simplifies the steps taken to design and build a molecular diagnostic laboratory system. At step 202, an orderable procedure is received. The orderable procedure may be selected from a list of orderable procedures by a user, such as a database administrator. The user identifies the orderable procedure for which they are building a system representation.

At step 204, the orderable procedure is associated to a discrete ontology concept. This is a concept that is a uniquely identified molecular entity that is part of an ontology, such as the ontology for genomic concepts described in commonly assigned U.S. application Ser. No. 11/028,262 entitled "Computerized System and Method for Creating and Maintaining an Ontology for Genomics Concepts". For example, a discrete ontology concept may be a human gene. Other discrete concepts may include the discrete concepts identified above in the discussion of an ontology for genomic concepts, a chemistry panel or other clinical test. At step 206, an election to build the system representation of test components associated with the discrete ontology concept and orderable procedure.

At step 208, the relationship path through an ontology, such as an ontology for genomic concepts, is traversed to identify test components for the ontology concept. In other words, the system uses the defined set of relationships between concepts in the ontology to traverse the ontology for the discrete gene concept associated with the orderable procedure to identify test components. Test components may include assays, tests to be performed for a particular screening or orderable procedure or likely results for an orderable procedure. For example, if the ontology is traversed for relationships for a discrete gene concept, the test components would be clinically significant gene mutations (such as nucleotide variants). The test components are displayed at step 209. The selection of likely results or test components for the orderable procedure is received at step 210. For example, a database administrator selects the test components that will be appropriate for their local institution. At step 212, based on the selections, a system representation for the orderable procedure is built based on the selections.

Figure 3:
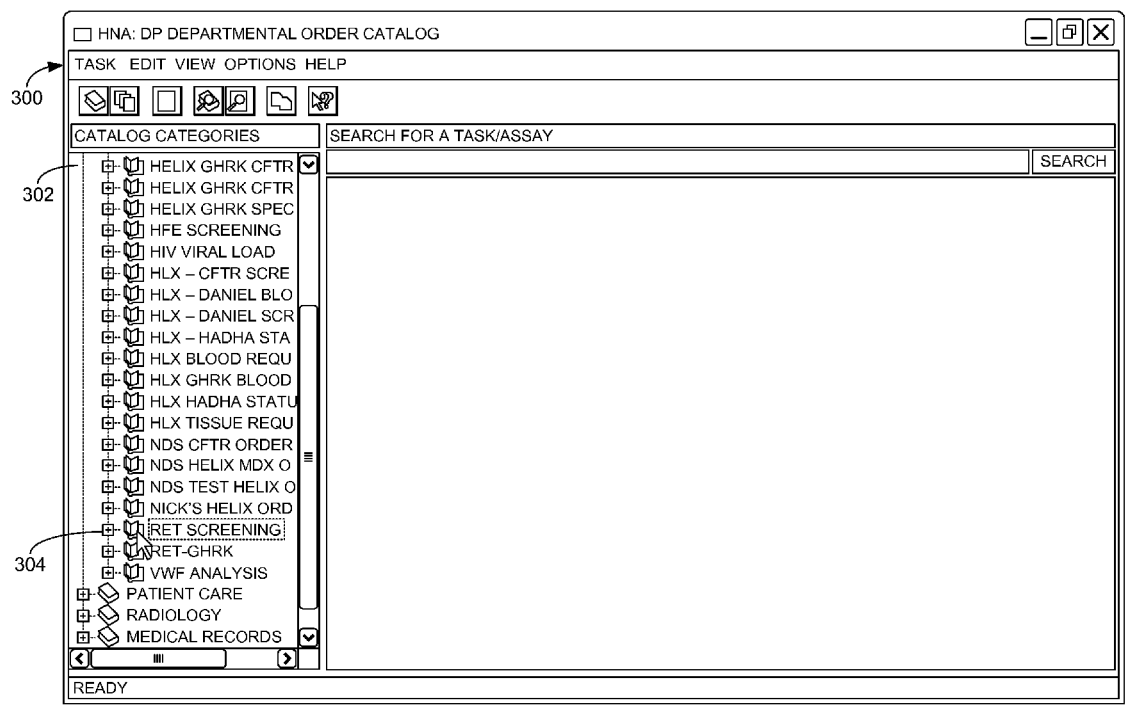
FIG. 3 is a screen displaying a departmental order catalog and selection of an orderable in accordance with an embodiment of the present invention.
Figure 4:
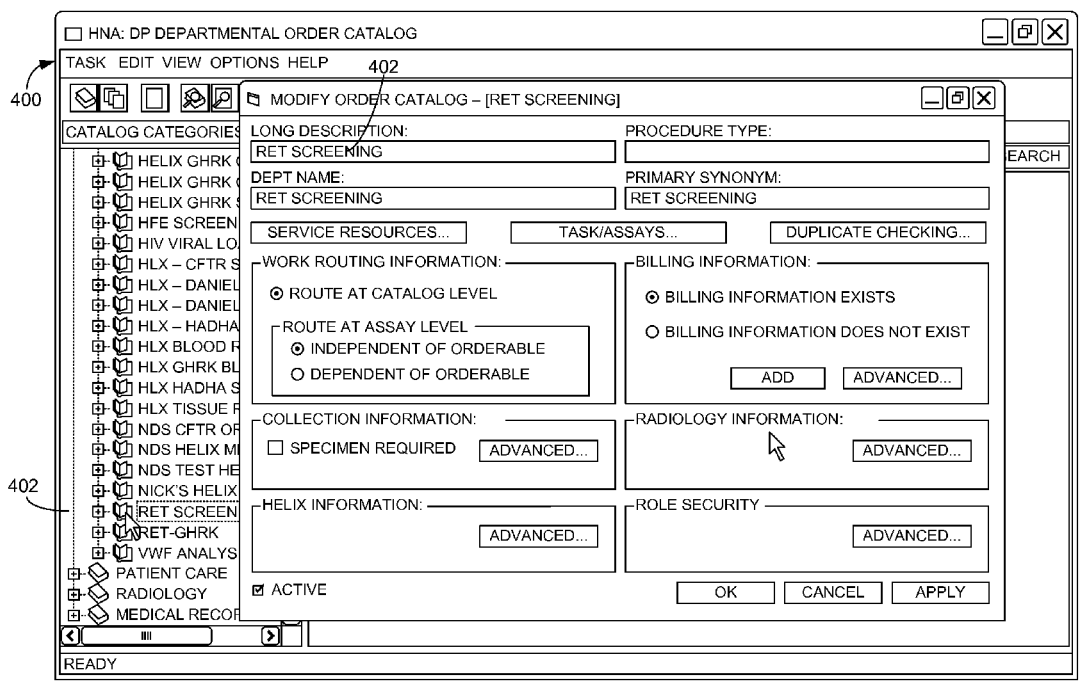
FIG. 4 is a screen displaying details of an orderable in accordance with an embodiment of the present invention.
Figure 5:
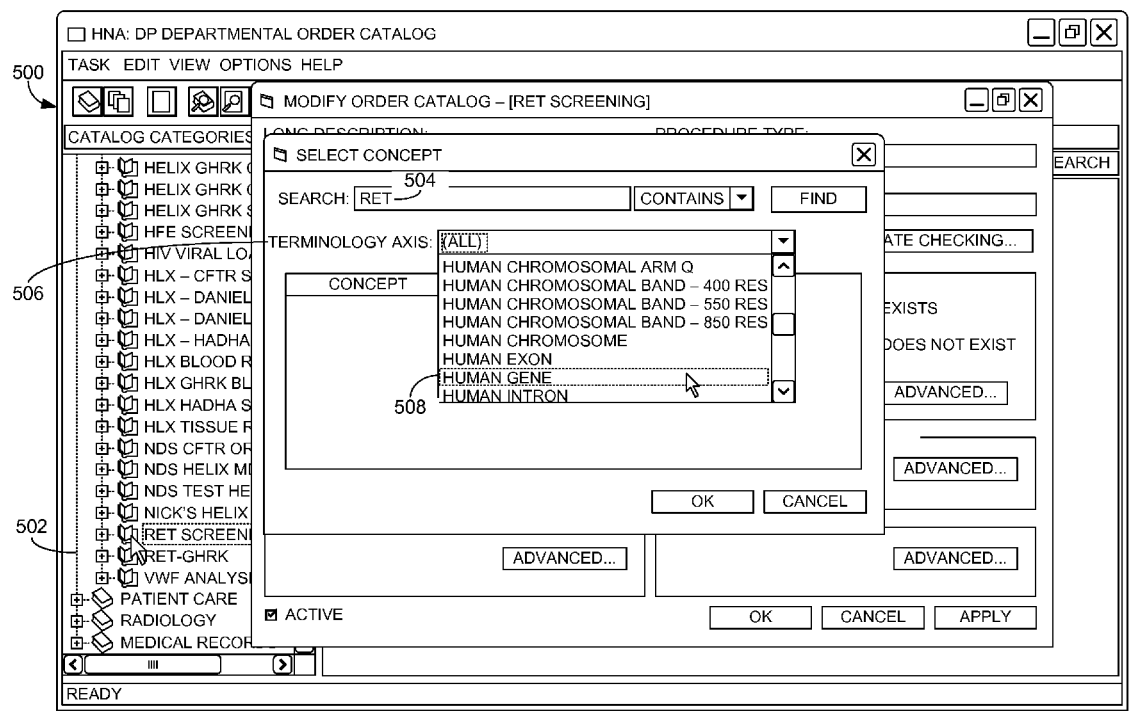
FIG. 5 is a screen displaying association of an orderable to a navigational ontology concept in accordance with an embodiment of the present invention.

By way of example, and not by limitation, with reference to FIG. 3, a screen 300 listing orderable procedures 302 is shown. The orderable procedures include diagnostic screening for particular molecular entities, such as CFTR screening and RET screening. In FIG. 3, the orderable procedure 304 for RET screening is selected by a user. With reference to FIG. 4, a screen 400 displaying details for the RET screening 402 is shown. With reference to FIG. 5, a display 500 showing association of an orderable 502 for RET screening with a discrete ontology concept 504 is shown. In this example, the association is done by searching for the RET orderable procedure 504 and selecting a navigational concept 506 for the orderable procedure at the terminology axis level. In this example the human gene navigational concept 508 has been selected by a user.

Figure 6:
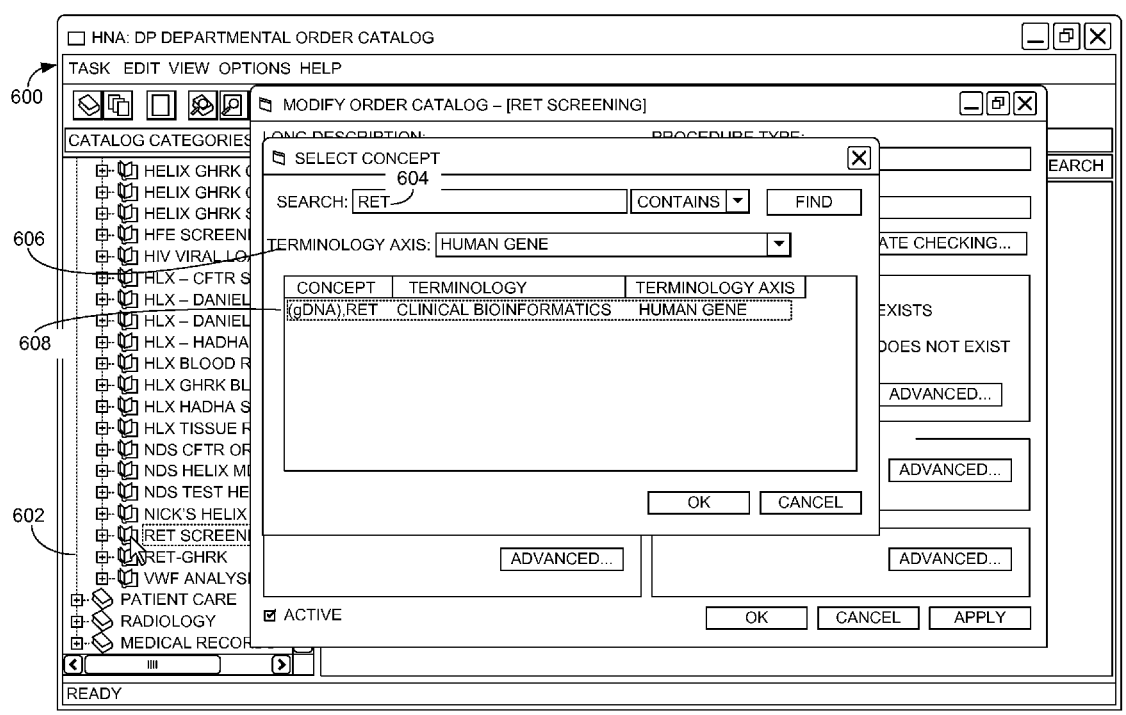
FIG. 6 is a screen displaying the association of an orderable with a navigational ontology concept in accordance with an embodiment of the present invention.

With reference to FIG. 6, a screen 600 displays that the RET screening orderable procedure 604 has been associated with the discrete human gene concept (gDNA)RET 608. The screen also displays that the RET screening orderable procedure 604 has been associated with the human gene navigational concept 606. Based on the association of the RET screening orderable procedure with the discrete concept (gDNA)RET 608, the ontology for discrete gene concept (gDNA)RET is traversed. Using the defining biological relationships of the ontology between discrete concepts, the likely results or test components for (gDNA)RET can easily be determined. In this example, the test components for (gDNA)RET are clinically significant gene mutations (such as nucleotide variants) for (gDNA)RET.

Figure 7:
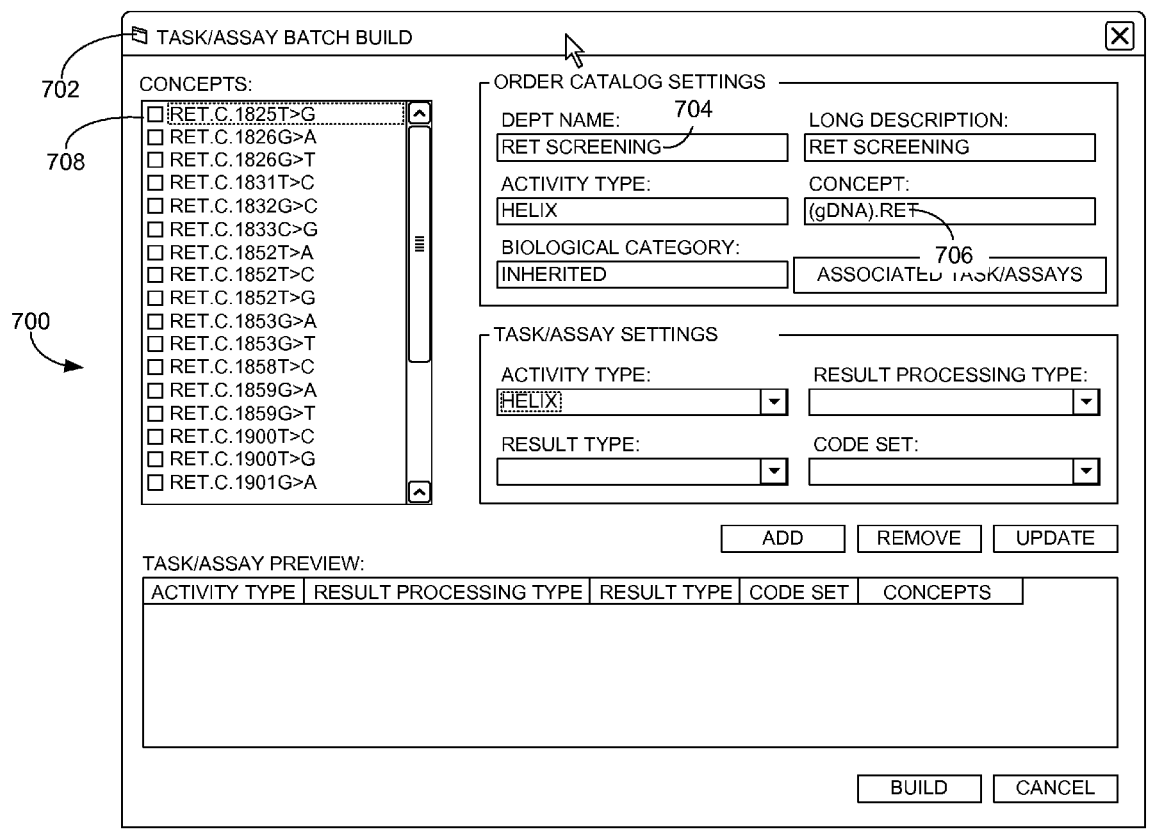
FIG. 7 is a screen displaying possible molecular diagnostic tests for the discrete concept for the orderable in accordance with an embodiment of the present invention.

FIG. 7 is a screen 700 displaying the test components 708 in a task/assay batch build 702 for the discrete human gene concept (gDNA)RET 706 associated with the RET screening orderable 704. The likely results or test components for the discrete human gene concept (gDNA)RET 706 include tests for nucleotide variants such as RET.c.1825T>G and RET.c.1826G>A.

Figure 8:
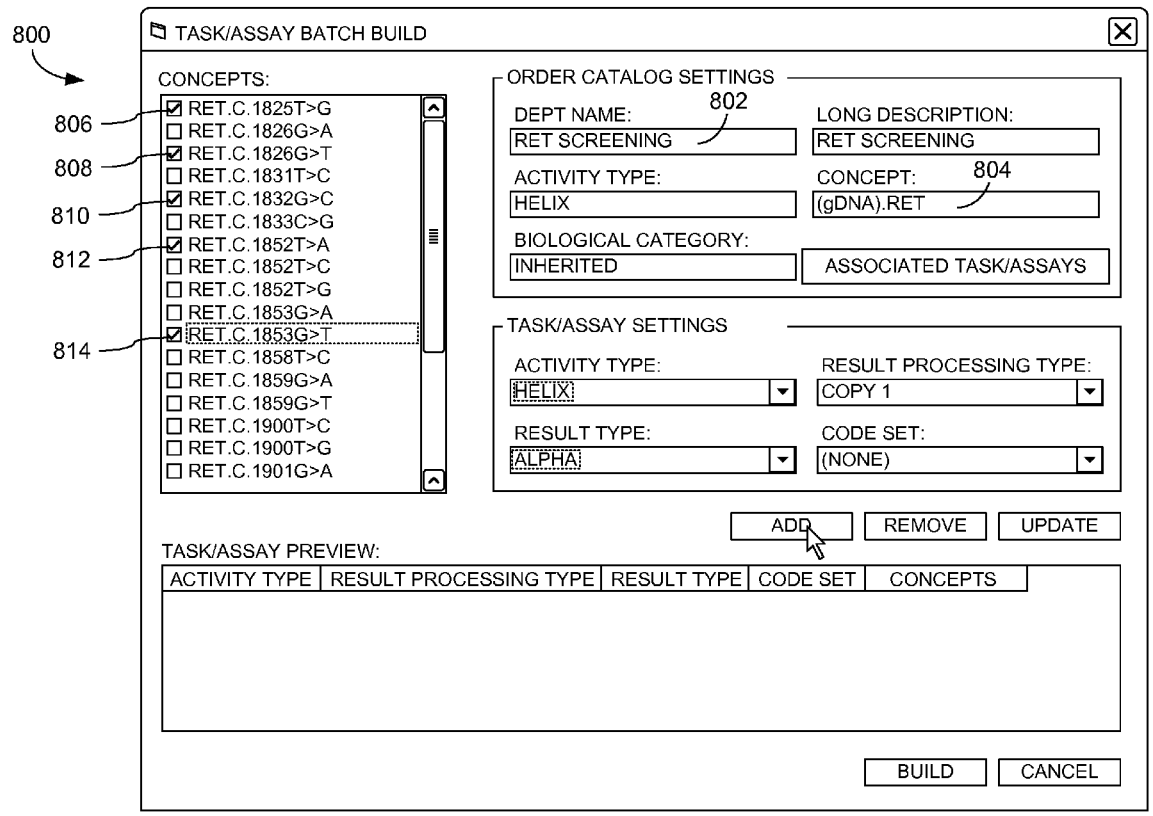
FIG. 8 is a screen showing selection of molecular diagnostic tests associated with the discrete concept associated with the orderable in accordance with an embodiment of the present invention.

With reference to FIG. 8, a screen 800 displaying the selection by a user of test components is shown. The user has selected the test components 806, 808, 810, 812 and 814 for discrete human gene concept (gDNA)RET 804 for the RET screening orderable procedure 802. The tests components selected include nucleotide variants: RET.c.1825T>G (806); RET.c.1826G>T (808); RET.c.1832G>C (810); RET.c.1852T>A (812); and RET.c.1853G>T (814).

Referring next to FIG. 9, is a display 900 for building a system representation of test components for an orderable procedure. The likely results or test components selected 906 are added to a task/assay list 908 for the discrete human gene concept (gDNA)RET 904 associated with the RET screening orderable procedure 902. Thus, in this example, the assays/test components 910 to be preformed for the RET screening orderable procedure are RET.c.1825T>G, RET.c.1826G>T, RET.c.1832G>C, RET.c.1852T>A and RET.c.1853G>T. In other words, these are the likely significant genetic mutations that will be tested for when an RET screening orderable procedure is ordered for a patient.

The present invention has been described in relation to particular embodiments, which are intended in all respects to be illustrative rather than restrictive. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations, and are contemplated within the scope of the claims. Not all steps listed in the various figures need to be carried out in the specific order described.

The invention claimed is:

1. A computer storage medium having embodied thereon computer-readable instructions that, when executed by a computing device, enable the computing device to perform a method of identifying a test component that is usable to perform an orderable healthcare procedure, the method comprising:
   receiving as an input the orderable healthcare procedure, wherein the orderable healthcare procedure is associated with a particular molecular entity;
   displaying on a device a navigational concept that represents a parent tier in an ontology hierarchy;
   responsive to input of the navigational concept, identifying a uniquely identified molecular entity that relates to the particular molecular entity and that is a child concept of the navigational concept;
   traversing biological relationships of the uniquely identified molecular entity to identify a potential test component of a task, which is executed to carryout the orderable healthcare procedure;
   displaying the potential test component to enable selection thereof; and
   upon receiving input of the potential test component, displaying the potential test component as the test component of the task.

2. The computer storage medium of claim 1, wherein the orderable healthcare procedure is a diagnostic screening that detects an existence of the particular molecular entity in a sample.

3. The computer storage medium of claim 1, wherein the navigational concept is a sub-category within a human-genome tier of the ontology hierarchy.

4. The computer storage medium of claim 1, wherein the uniquely identified molecular entity is a specific human gene.

5. The computer storage medium of claim 1, wherein biological relationships link the specific human gene with a nucleotide variant of the specific human gene.

6. The computer storage medium of claim 5, wherein the nucleotide variant is used to identify the potential test component.

7. The computer storage medium of claim 5, wherein the horizontal defining biological relationships span one or more parent-child relationships.

8. The computer storage medium of claim 7, wherein the horizontal defining biological relationship is a known biological relationship between two molecular entities.

9. A computerized system for identifying test components, which are usable to perform an orderable healthcare procedure, the system comprising a processor coupled to computer-storage media that comprises:

a receiving component that receives an input of the orderable healthcare procedure, wherein the orderable healthcare procedure is associated with a particular molecular entity;

an associating component that, upon input of a navigational concept, associates the orderable healthcare procedure with a discrete ontology concept,
   (1) wherein the navigational concept includes a category of molecular entities that is a parent concept of said discrete ontology concept, and
   (2) wherein the discrete ontology concept includes a uniquely identified molecular entity, a traversing component that traverses an ontology of the discrete ontology concept to identify test components related to the discrete ontology concept, wherein the ontology comprises horizontal defining biological relationships associating the discrete ontology concept with the test components; and a displaying component for displaying identified test components related to the discrete ontology concept.

10. The system of claim 9, further comprising a second receiving component that receives an input of the identified test components.

11. The system of claim 10, further comprising a building component that, based on the input of the identified test components, builds a system of test components that are usable to carry-out the orderable procedure.

12. The system of claim 9, wherein the test components are discrete concepts within the ontology.

13. The system of claim 12, wherein the test components are clinically significant gene mutations.

14. The system of claim 13, wherein the test components are related to the discrete ontology concept by horizontal defining biological relationships and wherein the horizontal defining biological relationships span one or more parent-child hierarchies.

15. The system of claim 14, wherein the horizontal defining biological relationship is a known biological relationship between two molecular entities.

16. The system of claim 9, wherein the ontology is an ontology of genomic concepts.

17. A method, which is implemented using a computing device, of identifying a test component that is usable to perform an orderable healthcare procedure, the method comprising:

receiving as an input the orderable healthcare procedure, wherein the orderable healthcare procedure is associated with a particular molecular entity;

displaying on a display device a navigational concept that represents a parent tier in an ontology hierarchy;

responsive to input of the navigational concept, identifying by a processor a uniquely identified molecular entity that relates to the particular molecular entity and that is a child concept of the navigational concept;

traversing biological relationships of the uniquely identified molecular entity to identify by the processor a potential test component of a task, which is executed to carry-out the orderable healthcare procedure;

displaying the potential test component to enable selection thereof; and upon receiving input of the potential test component, displaying the potential test component as the test component of the task.

18. The method of claim 17, wherein the orderable healthcare procedure is a diagnostic screening that is usable to detect an existence of the particular molecular entity in a sample.

19. The method of claim 17, wherein the navigational concept is a subcategory within a human-genome tier of the ontology hierarchy.

20. The method of claim 17, wherein the uniquely identified molecular entity is a specific human gene.

* * * * *